(12) United States Patent
Wadström

(10) Patent No.: US 7,837,865 B2
(45) Date of Patent: Nov. 23, 2010

(54) CONTAINER FOR PURIFYING WATER BY UTILIZATION OF SUNLIGHT

(76) Inventor: Petra Wadström, Västerhomsvägen 22, SE-184 60 Åkersberga (SE)

(*) Notice: Subject to any disclaimer, the term of this patent is extended or adjusted under 35 U.S.C. 154(b) by 852 days.

(21) Appl. No.: 11/791,449

(22) PCT Filed: Dec. 1, 2005

(86) PCT No.: PCT/SE2005/001814
§ 371 (c)(1),
(2), (4) Date: May 24, 2007

(87) PCT Pub. No.: WO2006/059948
PCT Pub. Date: Jun. 8, 2006

(65) Prior Publication Data
US 2007/0262010 A1 Nov. 15, 2007

(30) Foreign Application Priority Data
Dec. 2, 2004 (SE) .................................. 0402941

(51) Int. Cl.
*C02F 1/32* (2006.01)
(52) U.S. Cl. .................... 210/85; 210/192; 210/748.11; 210/464; 210/473; 210/475
(58) Field of Classification Search .................. None
See application file for complete search history.

(56) References Cited

U.S. PATENT DOCUMENTS

| | | | | |
|---|---|---|---|---|
| 2,369,232 A | * | 2/1945 | Hinton | 210/198.1 |
| 2,389,185 A | * | 11/1945 | Dick | 210/472 |
| 2,738,105 A | * | 3/1956 | Ogden et al. | 222/189.08 |
| 2,788,919 A | * | 4/1957 | Bostwick | 222/129 |
| 2,826,338 A | * | 3/1958 | Davis | 222/129 |
| 3,154,219 A | * | 10/1964 | Dean et al. | 222/129 |
| 3,323,684 A | * | 6/1967 | Furrer et al. | 210/474 |
| 3,335,917 A | * | 8/1967 | Knight | 222/189.07 |
| 4,239,032 A | * | 12/1980 | Irving | 126/640 |
| 4,520,793 A | * | 6/1985 | Hall | 126/626 |
| 4,557,251 A | * | 12/1985 | Burkhardt | 126/640 |
| 4,696,284 A | * | 9/1987 | Stowell | 126/640 |
| D292,267 S | * | 10/1987 | Costa | D9/747 |
| D292,268 S | * | 10/1987 | Costa | D9/741 |

(Continued)

FOREIGN PATENT DOCUMENTS

CN 2553305 5/2003

(Continued)

*Primary Examiner*—Robert James Popovics
(74) *Attorney, Agent, or Firm*—Dickstein Shapiro LLP

(57) ABSTRACT

The present invention relates to a container (2) for purifying water by utilization of sunlight, comprising a first surface (4, 8', 9', 10', 12') that is formed of a permeable layer for sunlight and a second surface (6, 8", 9", 10", 12") that is formed of an absorbing layer for sunlight. Further, the container comprises a first opening (14) and a second opening (16), respectively, provided with filter elements (18, 19). Filling with water is intended to be done in the first opening (14) and discharge of water is intended to be done through the second opening (16) after the water in the container (2) has been heated to a temperature of at least 600 C after exposure by sunlight and also exposure of ultraviolet radiation in order to make it possible to kill undesired micro-organisms.

5 Claims, 1 Drawing Sheet

U.S. PATENT DOCUMENTS

| | | | | |
|---|---|---|---|---|
| 4,881,652 | A * | 11/1989 | Schiemann | 220/23.8 |
| 4,994,186 | A * | 2/1991 | Hays | 210/464 |
| D315,829 | S * | 4/1991 | Covington | D3/202 |
| 5,022,547 | A * | 6/1991 | Spangler et al. | 220/23.4 |
| 5,167,819 | A * | 12/1992 | Iana et al. | 210/474 |
| D338,405 | S * | 8/1993 | Charbonneau et al. | D9/520 |
| D341,085 | S * | 11/1993 | Charbonneau et al. | D9/524 |
| 5,415,774 | A * | 5/1995 | Cowan et al. | 210/266 |
| D378,191 | S * | 2/1997 | Wehrle et al. | D9/742 |
| 5,681,463 | A * | 10/1997 | Shimizu et al. | 210/266 |
| 5,692,626 | A * | 12/1997 | Wehrle et al. | 215/6 |
| D390,115 | S * | 2/1998 | Wehrle et al. | D9/528 |
| D394,805 | S * | 6/1998 | Kafzan et al. | D9/740 |
| 6,311,877 | B1 * | 11/2001 | Yang | 222/510 |
| 6,344,146 | B1 * | 2/2002 | Moorehead et al. | 210/668 |
| 6,395,170 | B1 * | 5/2002 | Hughes et al. | 210/232 |
| 6,569,329 | B1 * | 5/2003 | Nohren, Jr. | 210/282 |
| 6,622,718 | B1 * | 9/2003 | Lu | 126/640 |
| 6,689,279 | B1 * | 2/2004 | Train | 210/800 |
| 7,090,072 | B1 * | 8/2006 | Elliott | 206/15.3 |
| 7,169,311 | B2 * | 1/2007 | Saccomanno | 210/198.1 |
| D559,119 | S * | 1/2008 | Stengel | D9/742 |
| D569,737 | S * | 5/2008 | Ogawa et al. | D9/740 |
| D569,738 | S * | 5/2008 | Ogawa et al. | D9/741 |
| 7,534,356 | B2 * | 5/2009 | Saccomanno | 210/748.11 |
| 7,713,483 | B2 * | 5/2010 | Maiden | 422/101 |
| 2003/0086848 | A1 * | 5/2003 | Saccomanno | 422/292 |
| 2004/0222163 | A1 * | 11/2004 | Saccomanno | 210/748 |
| 2005/0189290 | A1 * | 9/2005 | Maiden | 210/473 |
| 2007/0262010 | A1 * | 11/2007 | Wadstrom | 210/175 |
| 2010/0102002 | A1 * | 4/2010 | O'Brien et al. | 210/668 |

FOREIGN PATENT DOCUMENTS

| | | |
|---|---|---|
| GB | 2 040 436 | 8/1980 |
| WO | WO 9805594 A1 * | 2/1998 |
| WO | WO 01/28933 | 4/2001 |
| WO | WO 02/066905 A2 | 8/2002 |

* cited by examiner

CONTAINER FOR PURIFYING WATER BY UTILIZATION OF SUNLIGHT

TECHNICAL AREA

The present invention relates to a container for purifying water by utilization of sunlight.

BACKGROUND

Contaminated drinking water is frequent and a large problem in many parts of the world, particularly in developing countries. 1.1 billion people are without reliable drinking water and 1.6 billion are lacking electricity. There is a great demand for being able to purify drinking water in a simple way. Following natural disasters, at war and other large catastrophes such as Aids epidemics, which often leaves children without their parents, the problems with purification of water often culminates and causes usually serious diarrhoea diseases. WHO has provided a standard that disinfecting systems have to fulfil in order to be considered acceptable. This standard requires that a system shall manage to treat water with 100000 colon forming bacillus (colony forming units—CFU) of *E-coli* per 100 ml water and from this produce water less than one (1 part) CFU per 100 ml.

It is previously known apparatuses and methods for purifying drinking water from harmful parasites and micro-organisms, which known apparatuses/methods utilises UV-light and/or heating to a temperature above 60° C. during about 1 h for pasteurization of the water. Natural sunlight contains UV-light and large amounts of heat energy. It is also known, to use simple pieces of cloth to filter out micro-organisms that usually are combined with larger particles. In common with most of the known apparatuses is that they comprises many and expensive components, are relatively complicated and/or have not a suitable construction that ensures a guaranteed purification of the water.

Through EP-A1-1106188 is previously known a container and a method for disinfection of drinking water. The container is preferably shaped of a flexible plastic material, such as a plastic bag. One side of the container comprises a UV-transparent layer and a second side comprises a layer that produces heat at exposure in sunlight. The container comprises a sealable opening that is used for discharging and filling of water.

DESCRIPTION OF THE INVENTION

One object with the present invention is to achieve a container for purifying water that at least partially eliminates those drawbacks that are associated with apparatuses according to the state of the art. A further object is that the purifying of water in the container according to the present invention should fulfil WHO standard. An additional object is to achieve a container that to high degree ensures purifying of water in the container, that is simple to use, easy to distribute and cheap to produce.

This object is achieved with a container for purifying of water by utilization of sunlight according to the present invention as defined in claim 1, which comprises a first surface that is formed of a permeable layer for sunlight and a second surface that is formed of an absorbing layer for sunlight. The second absorbing surface is composed of up to about ⅔-parts of the delimiting surfaces of the container. Further the container comprises a first sealable opening and a second sealable opening, respectively. The respective opening is provided with filter elements, whereby filling with water is intended to be done in the first opening and discharge of water is intended to be done through the second opening after the water in the container has been heated to a temperature of at least 60° C. after exposure by sunlight and also exposure of ultraviolet radiation in order to make it possible to kill undesired micro-organisms.

By those means, it is achieved that the one of the sides of the container, which container is filled with water, that is to be placed against the sunlight, is suitably shaped of a completely transparent layer, in order to allow a maximum of sunlight to pass to shine through the water, and the other side of the container is of an absorbing material, a so called absorber, which absorbing layer is hit by the sunlight. This absorber may substantially be composed of a black surface. The sunlight hits the absorber, whereby conversion to heat energy takes place through emission. The water temperature increases fast and the heat is kept in the container. The water is also exposed for UV-radiation and kills undesired micro-organisms and disinfects in that way the water.

The two openings on the container that each are provided with a respective filter element, implies that the risk for contamination of the water in the container can be minimised. Thanks to that one opening is intended for discharge and one for filling of water, it can by those means be achieved that purified water in the container is not discharged through an opening for filling of water, which can re-contaminate the water as a consequence of those micro-organisms, which were separated at the filling, that can be left on the filter elements. Owing to that the opening for discharge of water also comprises a filter element, it is achieved that the water in the container becomes sealed, and thus means a safety that the water neither is contaminated through introduction of micro-organisms, parasites and also larger impurities through the discharge opening. One advantage with the solution according to the present invention is that the container can be formed with a shape, such as for instance a relatively flat design, which is most preferably according to an embodiment of the present invention in order to facilitate that the UV-radiation meets as large radiation surface as possible for disinfection of micro-organisms in the water. A shallow/flat shaping makes it also easy to store, transport, distribute, handle and can be shaped with a attractive design. Yet an advantage is that the present invention eliminates the need for chemical additives, electricity and complicated techniques of containers for purifying of water, at the same time as the purified water in the container can fulfil the demands according to the WHO standard. The container is refillable and can be produced to a low cost. The container according to the invention also creates the possibility for an easy distribution and uncomplicated handling for the end user thanks to the ability to stack them.

The first surface that is formed of a layer for transmitting the sunlight is suitably formed of a transparent, see-through material such as a plastic that keeps its high degree of transparency, in order to let through a maximum of sunlight, during repeated use and thus not becomes turbid after a short time of use.

The whole container can be of the same material as the above mentioned first surface, suitably of plastic material, however where the second surface is formed of an absorbing layer for sunlight, and suitably not a transparent layer. The layer is suitably substantially black in its colour. Thus, the second surface of the container can be painted black, produced from black plastic material, can be provided with a black layer, a film that is pasted on the side or in similar way provided with a sunlight and UV-radiation absorbing layer. The second absorbing surface comprises suitably at least about half the delimiting surface of the container and up to about ⅔-parts of the delimiting surfaces of the container, which has been shown to provide a faster heating to a temperature of at least 60° C. after exposure by sunlight compared to if only one fourth to one third of the container is of absorbing material. The first sunlight pervious surface is composed of suitably up to about half the delimiting surface of the container.

Coarser impurities are separated by deposition on the filter when contaminated water is filled in the first opening. At the discharge of water, the second opening is used since impurities can be present on the filter of the first opening for the filling. Also the second opening for discharge of water is provided with a filter in order to avoid that impurities are introduced in the container during discharge. By using two sealable openings, vacuum in the container can be avoided in such a way that a lid that seals the filling opening can be slightly opened to let in air, such that the purified water in the container can be poured out through the discharge opening. The openings may also comprise filters for purification of chemical substances.

Further advantages and features according to embodiments of the invention are evident from the claims, and also in the following from the description of the embodiments.

DESCRIPTION OF THE DRAWINGS

The present invention will now be described more in detail in embodiments, with reference to the attached drawings, without limiting the interpretation of the invention thereto, in which FIG. 1A in a perspective view schematically shows a container in accordance with the present invention, and FIG. 1B in an explanatory sketch shows sealable openings of an upper part of the container in FIG. 1.

DETAILED DESCRIPTION OF EMBODIMENTS

Figure 1A:
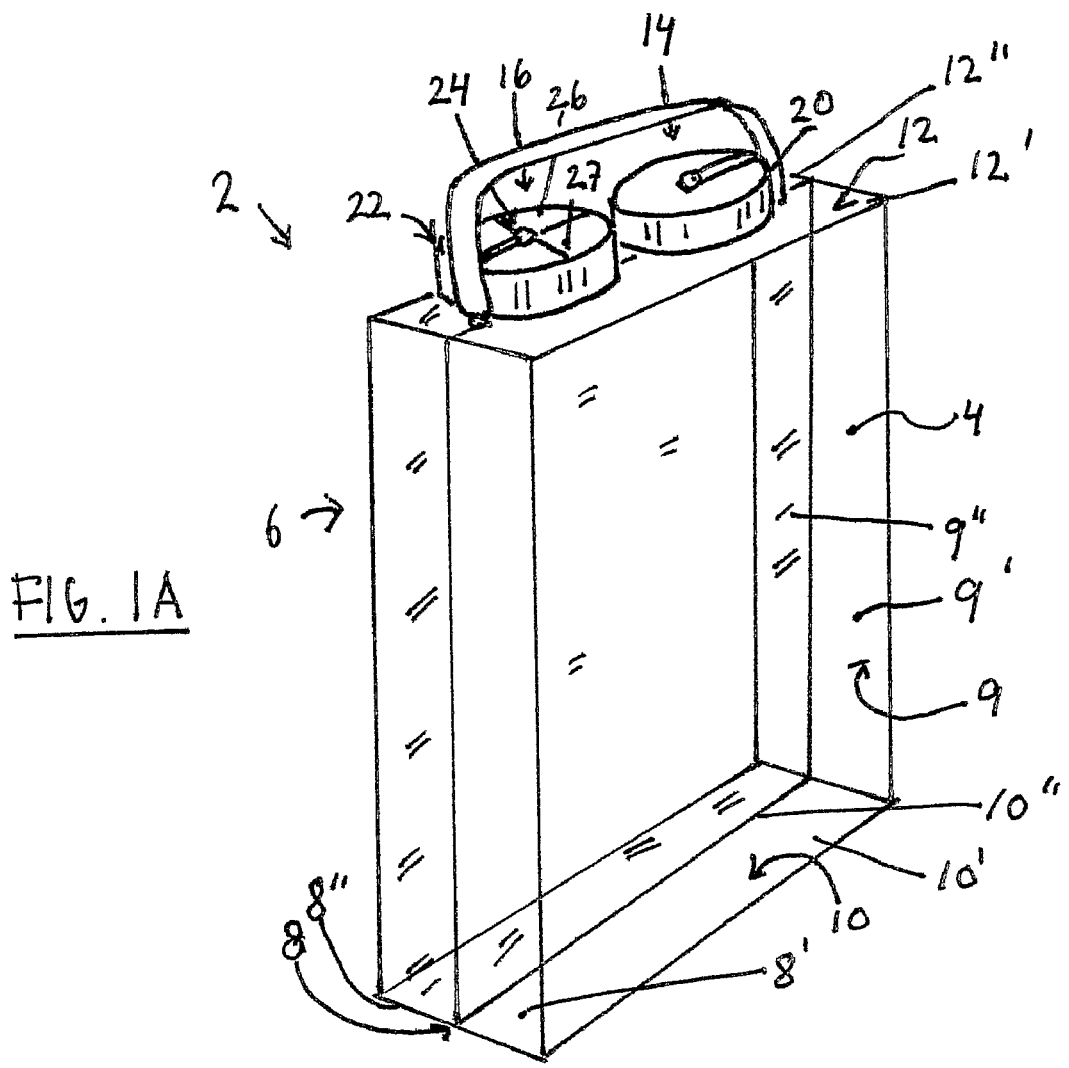
Figure 1B:
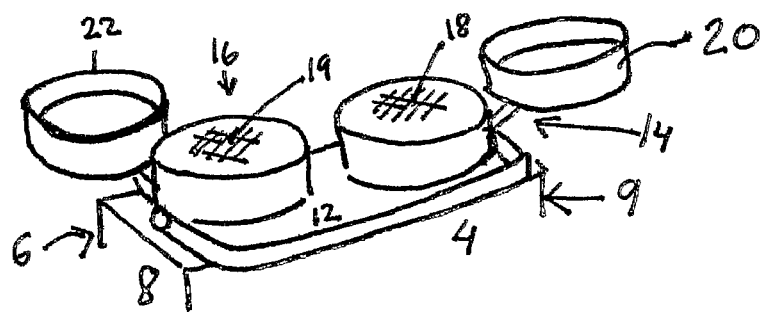

A container 2 for purifying water by utilization of sunlight is shown in FIG. 1, in accordance with the present invention. According to the embodiment in FIG. 1A-B, is a container 2 illustrated that comprises six sides, a first side 4, a second side 6 opposite the first side, two short sides 8,9, a bottom side 10 and a top side 12. In this way is a relatively shallow/flat container 2 formed that easily can be placed on the ground. By having a flat shaping, it is intended that the first and the second side 4, 6, respectively, have an essentially larger extension than the other sides 8-10, 12. A relatively flat form of the container also facilitates that the UV-radiation meets a relatively large radiation surface, i.e. a target area of the container, such that the water effectively and time efficiently is exposed for the UV-radiation and thereby facilitates at least some killing of micro-organisms. Within the scope of the inventive concept, the container may of course be of another shape, such as for example comprising more sides than six or be essentially cylindrical, although such a shape may imply that it is harder to place in correct position on the ground. In that respect, it is most preferred to have a relatively flat container, having plane sides, in accordance with the present invention. According to the present invention, the first sunlight permeable surface in the embodiment shown in FIG. 1A-B comprises the first surface 4, and also the halves 8', 9', 10', 12' of the short sides 8, 9, the bottom side 10 and the top side 12 that is adjacent to the first side 4. Further as evident from FIGS. 1A-B, the second sunlight permeable surface comprises the second side 6, and also the halves 8'', 9'', 10'', 12'' of the short sides 8, 9, the bottom side 10 and top side 12 that is adjacent to the second side 6. In accordance with the container 2 according to FIGS. 1A-B, the short sides 8, 9, the bottom side 10 and the top side 12 are in that respect half painted black adjacent the second side 6.

Further, the container comprises a first sealable opening 14 and a second sealable opening 16, respectively, provided with a respective filter element 18, 19, whereby filling with water is done in the first opening 14 and discharge of water is done through the second opening 16 after the water in the container 2 has been heated to a temperature of at least 60° C. after exposure by sunlight. The filter elements 18, 19 can suitably be fixed in the openings 14, 16, preferably fixed by welding, moulded or in similar way securely arranged in the openings. The respective filter element 18, 19, according to an embodiment of the present invention, may be arranged in a cylindrical house-formed body (not shown), provided with male threads, which is adapted to be screwed in the respective opening 14, 16, provided with corresponding female threads. The filter elements 18, 19 according to the present invention are preferably formed such that they accomplish closeness and a pore size that admits self-flowing, i.e. a high flow rate. The pore size can preferably be in the size of up to about 20 micrometer. One filter element 18, 19 according to the present invention is suitably composed of a screen cloth in the form of a closely woven cloth, net, membrane or the similar, for example of nylon or silk, which is securely moulded on the outermost edge of an opening 14, 16.

The first opening 14 may comprise a lid 20 for closing of the opening when water has been filled. The second sealable opening 16 can comprise a lid 22 which comprises indicator (s) that may be set for indication that the water in the container has been heated to a temperature of at least 60° C. after exposure by sunlight. The lid 22 can be provided with a knob 24 that comprises two differently coloured surfaces 26, 27, where one of the colours is set forward in order to indicate that the purification procedure has been carried out. The sides of the lids 20, 22 are suitably formed with sunlight permeable sides. Also the neck of the openings 14, 16 are semi UV-absorbing and semi UV-permeable in the embodiment shown in the FIGS. 1A-B.

A temperature indicator (not shown), such as a LCD temperature indicator, may suitably be arranged centrally in the container 2, which temperature indicator is arranged to indicate when, and that, the water in the container 2 has reached a temperature of at least 60° C. after exposure by sunlight. The temperature indicator can for instance be rod-shaped and arranged from one of the sides 4, 6, 8-9, 10, 12 directed against the centre of the container 2. Suitably the temperature indicator is arranged to change colour when the temperature reaches at least 60° C. The temperature indicator may suitably be provided with a memory such that a reached maximum temperature during the sunlight exposure can be checked afterwards. The temperature indicator may also be reset.

The UV-light kills DNA in the micro-organisms such that a bactericidal effect is facilitated. An example of dimensions of the container for a volume of 2 litres can e.g. be 23.5 cm high, 17 cm wide and a thickness of 5 cm, but the container may of course be of other dimensions. The sunlight, that by means of the sunlight absorbing surface, the so called absorber, converts the sunlight energy into heat energy and rapidly raises the temperature of the water when exposed to sunlight, whereby it also achieves a pasteurization effect when the temperature has reached about 60° C. During about 10 minutes the temperature should be kept at 60° C. or higher. When the exposure of sunlight is completed, the container should be cooled in the shadow or over the night such that the water should reach a drinkable temperature. The container according to the invention is suitably recyclable. In that respect it is suitable that during a cycle of a day and night, have at least three containers: one for collection and purification, one for cooling and one for consumption. Suitably also instructions of application should be present on the side of the container, conveniently on the outside of the container having the absorbing surface, e.g. in the form of a drawn instruction that is easily understandable irrespective of age, language or education.

The invention claimed is:

1. Container for purifying water by utilization of sunlight, comprising a first surface that is formed of a permeable layer for sunlight and a second surface that is formed of an absorbing layer for sunlight, characterised by that the second absorbing surface is composed of up to about ⅔-parts of the delimiting surfaces of the container, the container comprises a first sealable opening and a second sealable opening, respectively, the respective openings are provided with filter elements, whereby filling with water is intended to be done in the first opening and discharge of water is intended to be done through the second opening after the water in the container has been heated to a temperature of at least 60° C. after exposure by sunlight and also exposure of ultraviolet radiation in order to make it possible to kill undesired microorganisms.

2. Container according to claim 1, characterised by that the filter elements are fixed in the openings.

3. Container according to claim 1, characterised by that the second sealable opening comprises a lid which comprises indicators that may be set for indication that the water in the container has been heated to a temperature of at least 60° C. after exposure by sunlight.

4. Container according to claim 1, characterised by that a temperature indicator is arranged centrally in the container, which temperature indicator is arranged to indicate when the water in the container has reached a temperature of at least 60° C. after exposure by sunlight.

5. Container according to claim 1, characterised by that the second absorbing surface comprises at least about half the delimiting layer of the container.

* * * * *